United States Patent
Diolaiti

(10) Patent No.: US 12,023,803 B2
(45) Date of Patent: Jul. 2, 2024

(54) SYSTEMS AND METHODS FOR CONTROL OF STEERABLE DEVICES

(71) Applicant: Intuitive Surgical Operations, Inc., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 577 days.

(21) Appl. No.: 17/279,753

(22) PCT Filed: Oct. 1, 2019

(86) PCT No.: PCT/US2019/053953
§ 371 (c)(1),
(2) Date: Mar. 25, 2021

(87) PCT Pub. No.: WO2020/072415
PCT Pub. Date: Apr. 9, 2020

(65) Prior Publication Data
US 2022/0009084 A1    Jan. 13, 2022

Related U.S. Application Data

(60) Provisional application No. 62/741,338, filed on Oct. 4, 2018.

(51) Int. Cl.
*G06F 17/00*        (2019.01)
*A61B 34/35*        (2016.01)
(Continued)

(52) U.S. Cl.
CPC .............. *B25J 9/065* (2013.01); *A61B 34/35* (2016.02); *A61B 34/37* (2016.02);
(Continued)

(58) Field of Classification Search
CPC .......... B25J 9/065; A61B 34/35; A61B 34/37; A61B 2034/301; A61B 2034/306; A61B 34/30; G05B 19/4155; G05B 2219/45117
(Continued)

(56) References Cited

U.S. PATENT DOCUMENTS 6,380,732 B1    4/2002  Gilboa
6,389,187 B1    5/2002  Greenaway et al.
(Continued)

FOREIGN PATENT DOCUMENTS

WO    WO-2016191298 A1    12/2016
WO    WO-2017109986 A1    6/2017
(Continued)

OTHER PUBLICATIONS

Robotic Catheters for Beating Heart Surgery (Year: 2011).*
(Continued)

*Primary Examiner* — Ronnie M Mancho
(74) *Attorney, Agent, or Firm* — Haynes & Boone, LLP

(57) ABSTRACT

Systems and methods for controlling an elongate device are provided herein. In some embodiments, a robotic system may comprise a manipulator assembly configured to drive an elongate device and a control device configured to receive user input commanding the elongate device. The robotic system may also comprise a control system communicatively coupled to the manipulator assembly and the control device. The control system may be configured to monitor movement of the elongate device during a plurality of intervals, monitor user input received by the control device during the plurality of intervals, and adjust a property of the elongate device based on at least one of the monitored movement or the monitored user input.

20 Claims, 5 Drawing Sheets

(51) Int. Cl.
  *A61B 34/37* (2016.01)
  *B25J 9/06* (2006.01)
  *G05B 19/4155* (2006.01)
  *A61B 34/30* (2016.01)

(52) U.S. Cl.
  CPC .... *G05B 19/4155* (2013.01); *A61B 2034/301* (2016.02); *G05B 2219/45117* (2013.01)

(58) Field of Classification Search
  USPC .......................................................... 700/257
  See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 9,259,274 | B2 | 2/2016 | Prisco |
| 9,452,276 | B2 | 9/2016 | Duindam et al. |
| 11,344,376 | B2 * | 5/2022 | Diolaiti .............. A61M 25/0147 |
| 11,707,837 | B2 * | 7/2023 | Oleynik ............... B25J 15/0095 |
| | | | 700/250 |
| 11,738,455 | B2 * | 8/2023 | Oleynik ............... B25J 15/0095 |
| | | | 700/250 |
| 2006/0013523 | A1 | 1/2006 | Childers et al. |
| 2010/0256558 | A1 * | 10/2010 | Olson .................... A61B 34/77 |
| | | | 604/95.01 |
| 2016/0059412 | A1 * | 3/2016 | Oleynik ................... B25J 19/02 |
| | | | 700/250 |
| 2017/0265956 | A1 | 9/2017 | Carlson et al. |
| 2017/0281288 | A1 | 10/2017 | Au |
| 2018/0177383 | A1 | 6/2018 | Noonan et al. |
| 2018/0256262 | A1 | 9/2018 | Duindam et al. |
| 2019/0029770 | A1 * | 1/2019 | Bailey ..................... A61B 34/74 |
| 2019/0231449 | A1 * | 8/2019 | Diolaiti ................ A61B 1/0016 |
| 2020/0078096 | A1 * | 3/2020 | Barbagli ................ A61B 34/30 |
| 2020/0155252 | A1 * | 5/2020 | Diolaiti .................. A61B 34/35 |

FOREIGN PATENT DOCUMENTS

| | | |
|---|---|---|
| WO | WO-2018005928 A1 | 1/2018 |
| WO | WO-2018125917 A1 | 7/2018 |

OTHER PUBLICATIONS

Robotic Catheters for Beating Heart Surgery (Year: 2011) (Year: 2011).*
International Preliminary Report on Patentability for Application No. PCT/US2019/053953, dated Apr. 15, 2021, 09 pages.
International Search Report and Written Opinion for Application No. PCT/US2019/053953, dated Jan. 7, 2020, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

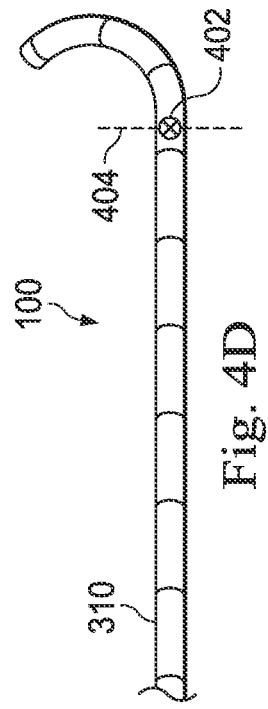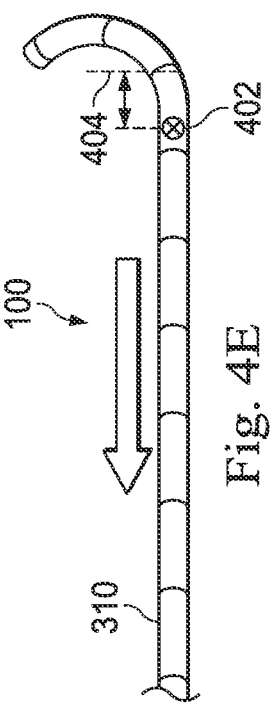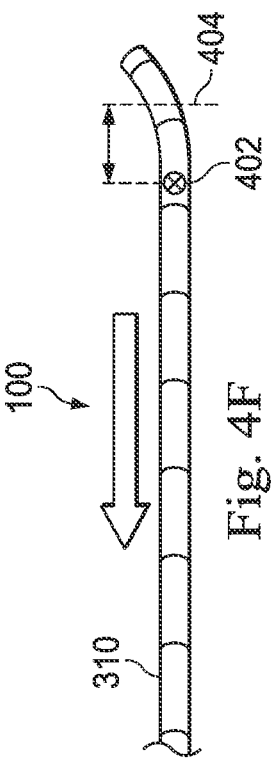
Fig. 4D  Fig. 4E  Fig. 4F
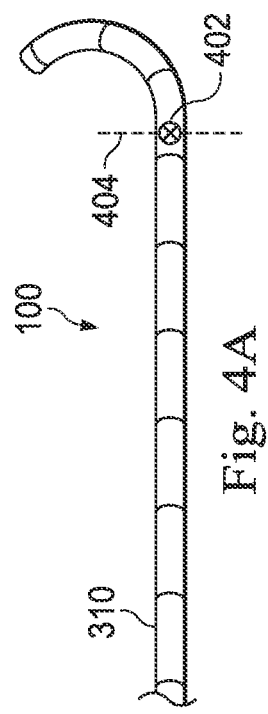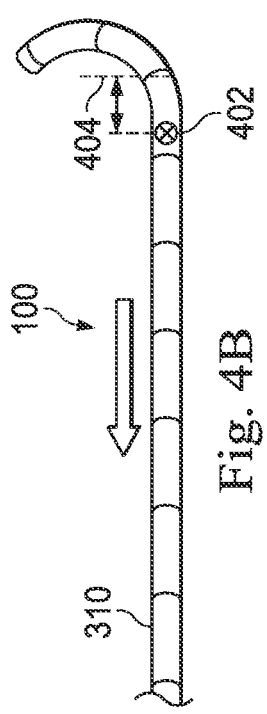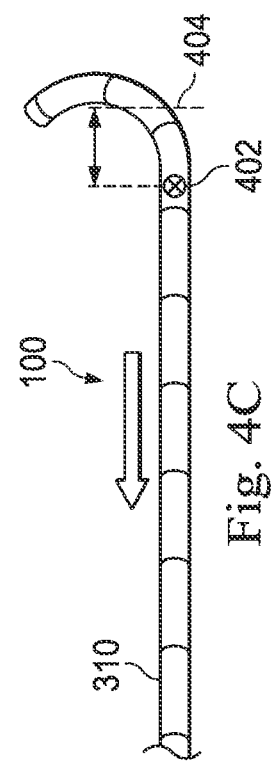
Fig. 4A  Fig. 4B  Fig. 4C

SYSTEMS AND METHODS FOR CONTROL OF STEERABLE DEVICES

CROSS-REFERENCE TO RELATED APPLICATIONS

This application is the U.S. national phase of International Application No. PCT/US2019/053953, filed Oct. 1, 2019, which designates the U.S. and claims priority to and the benefit of U.S. Provisional Application 62/741,338 filed Oct. 4, 2018, both of which are incorporated by reference herein in their entirety.

FIELD

Examples described herein relate to systems and methods for a procedure, such as systems and methods for controlling elongate devices.

BACKGROUND

Instruments can be used to manipulate and perform tasks in a work space. Such instruments may be configured to be supported and operated partially or entirely by manipulator assemblies. Such instruments and manipulator assemblies can be used to perform non-medical procedures or medical procedures. For example, medical tools or medical manipulators can be used to perform minimally invasive medical procedures. As another example, industrial tools or industrial manipulators can be used in manufacture or testing. As yet other examples, tools or manipulators can be used in procedures for entertainment, exploration, and various other purposes.

Minimally invasive medical techniques may generally be intended to reduce the amount of tissue that is damaged during invasive medical procedures, thereby reducing patient recovery time, discomfort, and harmful side effects. Such minimally invasive techniques may be performed through natural orifices in a patient anatomy or through one or more incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some medical and non-medical instruments (including manipulation instruments, imaging instruments or other sensing instruments, etc.) may be teleoperated or otherwise computer-assisted. When performing a procedure with a system using such an instrument, mechanisms are desired to control properties of the instrument, such as rigidity, in response to motion for the safety of the patient and/or the surrounding environment.

SUMMARY

The following presents a simplified summary of various examples described herein and is not intended to identify key or critical elements or to delineate the scope of the claims.

In one example, a robotic system may comprise a manipulator assembly configured to drive an elongate device and a control device configured to receive user input commanding the elongate device. The robotic system may also comprise a control system communicatively coupled to the manipulator assembly and the control device. The control system may be configured to monitor movement of the elongate device during a plurality of intervals, monitor user input received by the control device during the plurality of intervals, and adjust a property of the elongate device based on at least one of the monitored movement or the monitored user input. Adjustment of the property may include keeping the property of the elongate device substantially the same during the first interval, based on at least one of movement or user input during a first interval of the plurality of intervals. Adjustment of the property may include adjusting the property of the elongate device at a first rate during the second interval, based on at least one of movement or user input during a second interval of the plurality of intervals. Adjustment of the property may include adjusting the property of the elongate device at a second rate that is greater than the first rate during the third interval, based on at least one of movement or user input during a third interval of the plurality of intervals.

In another example, a method may include monitoring movement of an elongate device, receiving user input commanding motion of the elongate device, determining a mode of operation based on at least one of the monitored movement or the received user input, and adjusting a property of the elongate device based on a profile associated with the mode of operation. Adjusting the property of the elongate device may include maintaining the property of the elongate device substantially the same during a first interval, adjusting the property of the elongate device at a first rate during a second interval, and adjusting the property of the elongate device at a second rate that is different from the first rate during a third interval.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 4A-4F are simplified diagrams of a robotic medical system including a steerable elongate device at various points during a method according to some embodiments.

Figure 1:
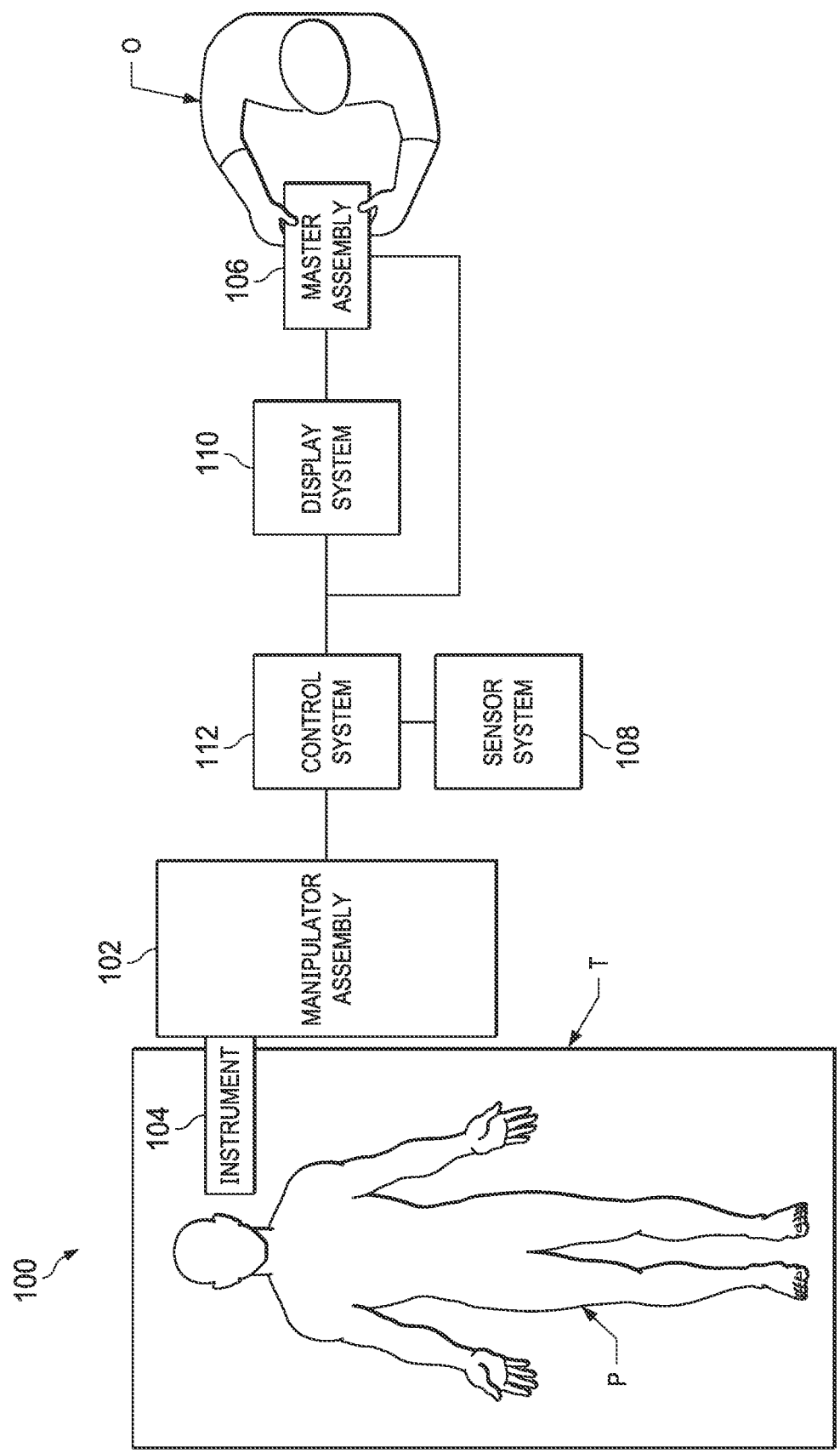
FIG. 1 is a simplified diagram of a medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The systems and techniques of the present application may provide safeguards for steerable instruments of a robotic system by monitoring movement, user input, and/or other factors and adjusting properties, such as rigidity, of the steerable instrument in response to the monitored factors. In some examples, the robotic system may monitor physical movement of the steerable instrument and user inputs commanding motion of the steerable instrument. When the movement and/or user input indicate that the steerable instrument is in a retraction mode, the system may reduce the rigidity of the instrument. The system may prioritize some factors over others so that actual physical retraction of the instrument might override user input or so that user input indicating retraction might override user input commanding steering of the instrument. The amount that the rigidity is affected, the rate of change in rigidity, and/or other aspects of the response may be determined according to one or more profiles associated with the monitored factors.

These examples are non-limiting, and other examples are described in detail below. Various aspects of the disclosed technology are described with respect to an example flexible robotic device or system, such as a robotically controlled catheter described with respect to FIGS. 1, 2A, and 2B. The disclosed technology for instrument control as described with respect to FIGS. 3-5 can be implemented to provide a number of advantages including improved safety of the patient and the surrounding environment in which the instrument is deployed.

FIG. 1 is a simplified diagram of a robotic medical system 100 according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used in robotic systems for animals, human cadavers, animal cadavers, portions of human or animal anatomy, non-surgical diagnosis, as well as for industrial systems and/or other general robotic systems.

As shown in FIG. 1, medical system 100 may include a manipulator assembly 102 for operating a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 may be mounted to and/or positioned near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is may be located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, scroll wheels, directional pads, buttons, data gloves, trigger-guns, hand-operated controllers, voice recognition devices, body motion or presence sensors, and/or the like.

Manipulator assembly 102 supports medical instrument 104 and may include a kinematic structure of one or more non-servo controlled links (e.g., one or more links that may be manually positioned and locked in place, generally referred to as a set-up structure), one or more servo controlled links (e.g., one or more links that may be controlled in response to commands from the control system), and/or a manipulator. Manipulator assembly 102 may include a plurality of actuators or motors that drive inputs on medical instrument 104 in response to commands from the control system (e.g., a control system 112). The actuators may include drive systems that when coupled to medical instrument 104 may advance medical instrument 104 into a naturally or surgically created anatomic orifice. Other drive systems may move the distal portion of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Medical system 100 may include a sensor system 108 with one or more sub-systems for receiving information about the manipulator assembly 102 and/or the medical instrument 104. Such sub-systems may include a position/location sensor system (e.g., an electromagnetic (EM) sensor system); a shape sensor system for determining the position, orientation, speed, velocity, pose, and/or shape of a distal portion and/or of one or more segments along a flexible body that may make up medical instrument 104; a visualization system for capturing images from the distal portion of medical instrument 104; and/or actuator position sensors such as resolvers, encoders, potentiometers, and the like that describe the rotation and orientation of the motors controlling the instrument 104.

Medical system 100 may include a display system 110 for displaying an image or representation of the surgical site and medical instrument 104. In some examples, display system 110 may present pre-operative or intra-operative images of a surgical site using image modalities such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In some embodiments, medical instrument 104 may include a visualization system that includes an image capture assembly to record a concurrent or real-time image of a surgical site and to provide the image to the operator O through one or more displays of display system 110.

In some examples, medical system 100 may configure the displayed representations, the medical instrument 104, and the controls of master assembly 106 such that the relative positions of the medical instruments are similar to the relative positions of the eyes and/or hands of operator O. In this manner, operator O can manipulate medical instrument 104 and hand controls as if viewing the workspace in substantially true presence.

In some examples, such as for purposes of image-guided medical procedures, display system 110 may display a virtual navigational image in which the actual location of medical instrument 104 is registered (e.g., dynamically referenced) with the preoperative or concurrent images/model. This may be done to present the operator O with a virtual image of the internal surgical site from a viewpoint of medical instrument 104.

Medical system 100 may also include control system 112. Control system 112 includes at least one memory and at least one computer processor (not shown) for effecting control between manipulator assembly 102, medical instrument 104, master assembly 106, sensor system 108, and/or display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions corresponding to processes disclosed herein and described in more detail below.

In some examples, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104.

Control system 112 may obtain sensor data from sensor system 108 that is used to compute an approximate location of medical instrument 104 with respect to the anatomy of patient P. The system may implement the sensor system 108 to register and display the medical instrument together with preoperatively or intraoperatively recorded medical images. For example, PCT Publication WO 2016/191298 (published Dec. 1, 2016 and titled "Systems and Methods of Registration for Image Guided Surgery"), which is incorporated by reference herein in its entirety, discloses example systems.

Medical system 100 may further include operations and support systems such as illumination systems, articulation (e.g., steering) control systems, irrigation systems, and/or suction systems (not shown). In some embodiments, medical system 100 may include more than one manipulator assembly and/or more than one master assembly. The exact number of manipulator assemblies may depend on the medical procedure and space constraints within the operating room, among other factors. Master assembly 106 may be co-located or they may be positioned in separate locations. Multiple master assemblies may allow more than one operator to control one or more manipulator assemblies in various combinations.

Figure 2A:
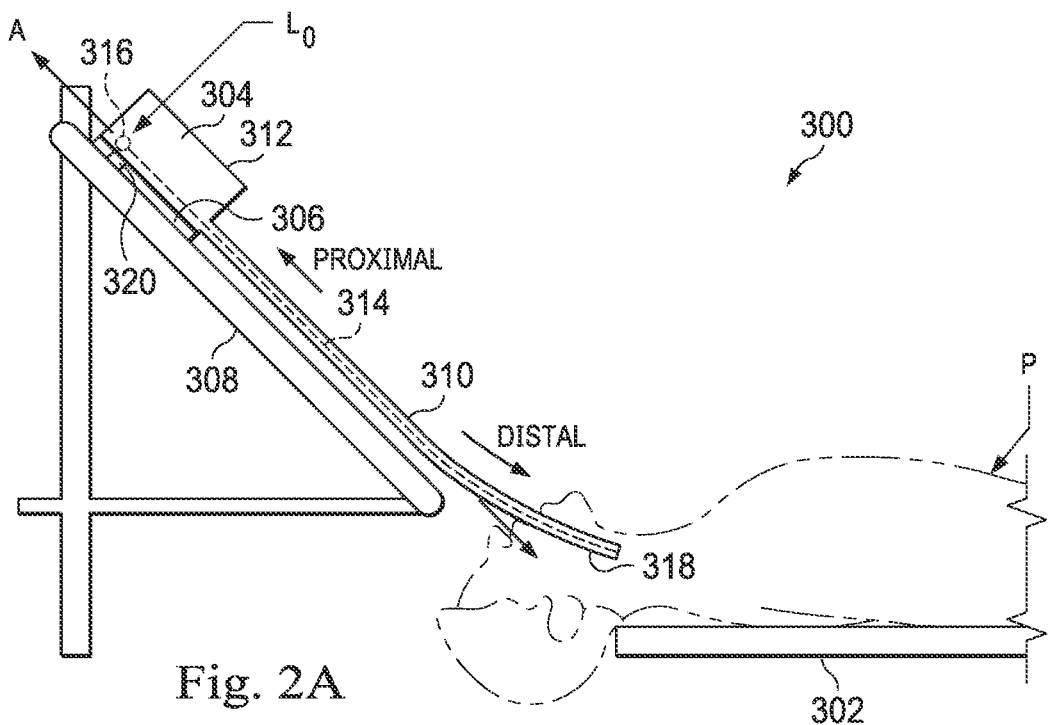
FIGS. 2A and 2B are simplified diagrams of side views of a patient coordinate space including a medical instrument mounted on an insertion assembly according to some embodiments.
Figure 2B:
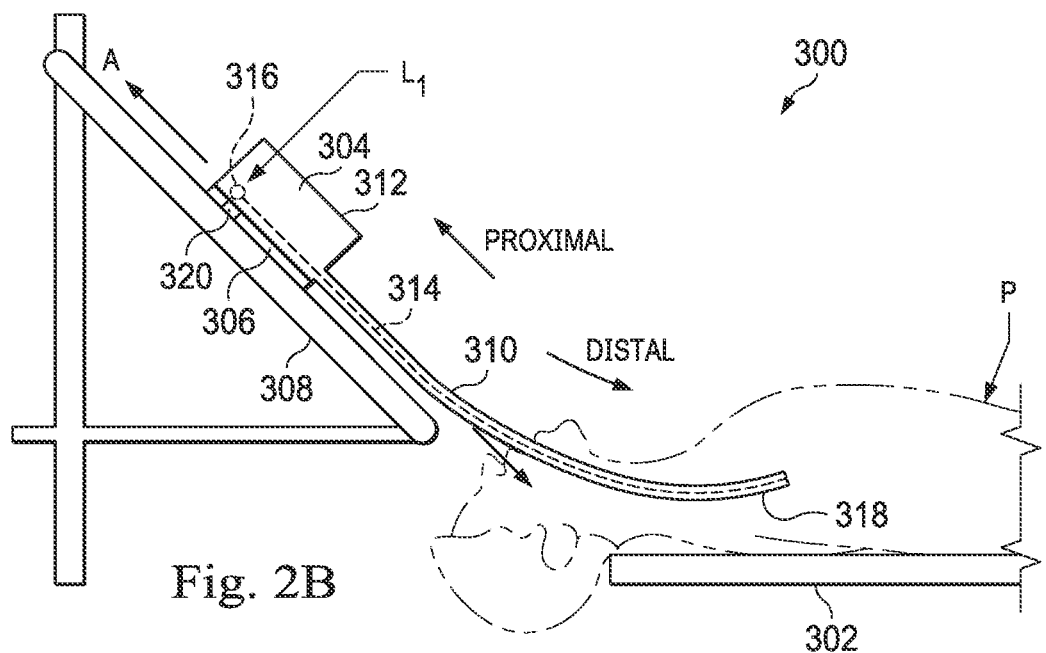

FIGS. 2A and 2B are simplified diagrams of side views of a patient coordinate space including a medical instrument mounted on an insertion assembly according to some embodiments. As shown in FIGS. 2A and 2B, a surgical environment 300 may include a patient P positioned on a table T. Patient P may be stationary within the surgical environment 300 in the sense that gross patient movement is limited by sedation, restraint, and/or other means. Cyclic anatomic motion including respiration and cardiac motion of patient P may continue. Within surgical environment 300, a medical instrument 304 is used to perform a medical procedure which may include, for example, surgery, biopsy, ablation, illumination, irrigation, suction, or a system registration procedure. The medical instrument 304 may be, for example, the instrument 104. The instrument 304 includes a flexible elongate device 310 (e.g., a catheter) coupled to an instrument body 312. Elongate device 310 includes one or more channels (not shown) sized and shaped to receive a medical tool (not shown).

Elongate device 310 may also include one or more sensors (e.g., components of the sensor system 108). In some examples, an articulation sensor 314, such as a fiber optic shape sensor, may be fixed at a proximal point 316 on instrument body 312. The proximal point 316 of the articulation sensor 314 may be movable with instrument body 312, and the location of the proximal point 316 may be known (e.g., via a tracking sensor or other tracking device). Articulation sensor 314 may measure a shape from the proximal point 316 to another point, such as distal portion 318 of the elongate device 310. Articulation sensor 314 may be aligned with the flexible elongate device 310 (e.g., provided within an interior channel (not shown) or mounted externally). In some examples, the optical fiber may have a diameter of approximately 200 μm. In other examples, the diameter may be larger or smaller. The articulation sensor 314 may be used to determine the shape of flexible elongate device 310. Optical fibers including Fiber Bragg Gratings (FBGs) may be used to provide strain measurements in structures in one or more dimensions. Various systems and methods for monitoring the shape and relative position of an optical fiber in three dimensions are described in U.S. patent application Ser. No. 11/180,389 (filed Jul. 13, 2005 and titled "Fiber optic position and shape sensing device and method relating thereto"); U.S. patent application Ser. No. 12/047,056 (filed on Jul. 16, 2004 and titled "Fiber-optic shape and relative position sensing"); and U.S. Pat. No. 6,389,187 (filed on Jun. 17, 1998 and titled "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. Various systems for using fiber optic sensors to register and display a surgical instrument with surgical images are provided in PCT Publication WO 2016/191298 (published Dec. 1, 2016 and titled "Systems and Methods of Registration for Image Guided Surgery"), which is incorporated by reference herein in its entirety.

In some examples, position sensors such as electromagnetic (EM) sensors, may be incorporated into the medical instrument 304. A series of position sensors may be positioned along the flexible elongate device 310 and used for shape sensing. In some examples, position sensors may be configured and positioned to measure six degrees of freedom, e.g., three position coordinates X, Y, Z and three orientation angles indicating pitch, yaw, and roll of a base point. In some examples, position sensors may be configured and positioned to measure five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999 and titled "Six-Degree of Freedom Tracking System Having a Passive Transponder on the Object Being Tracked"), which is incorporated by reference herein in its entirety.

Elongate device 310 may house cables, linkages, or other steering controls (not shown) that extend between instrument body 312 and distal portion 318 to controllably bend distal portion 318. In some examples, at least four cables are used to provide independent up-down steering to control a pitch of distal portion 318 and left-right steering to control a yaw of distal portion 318. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The instrument body 312 may include drive inputs that removably couple to and receive power from drive elements, such as actuators, of the assembly.

Instrument body 312 may be coupled to instrument carriage 306. Instrument carriage 306 may be mounted to an insertion stage 308 fixed within the surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to medical instrument 304 to control insertion motion (e.g., motion along the A axis) and/or motion of the distal portion 318 of the elongate device 310 in multiple directions such as yaw, pitch, and/or roll. Instrument carriage 306 or insertion stage 308 may include actuators, such as servomotors, (not shown) that control motion of instrument carriage 306 along insertion stage 308.

A sensor device 320, which may be a component of the sensor system 108, may provide information about the position of instrument body 312 as it moves on insertion stage 308 along an insertion axis A. Sensor device 320 may include one or more resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 2A shows the instrument body 312 and the instrument carriage 306 in a retracted position along insertion stage 308. In this retracted position, the proximal point 316 is at a position $L_0$ on axis A. In FIG. 2B, instrument body 312 and instrument carriage 306 have advanced along the linear track of insertion stage 308, and the distal portion 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 may be used to determine the position of proximal point 316 relative to position $L_0$. In some examples, this position may further be used as an indicator of the distance or insertion depth to which distal portion 318 of elongate device 310 is inserted into the passageway(s) of the anatomy of patient P.

As the elongate device 310 is advanced and retracted in the passageways, properties of the elongate device 310—such as the radial or axial rigidity (e.g., stiffness) of the elongate device 310—may be altered in order to facilitate movement and protect the passageways. For example, the rigidity of the distal portion 318 of the elongate device 310 may be increased when the device is advanced through a passageway to guide the device, to anchor the device in place, or to manipulate a deformable passageway. In contrast, the rigidity of the distal portion 318 of the elongate device 310 may be decreased when the device is retracted to reduce the force on the passageways, which may otherwise lead to abrasion or injury. In the course of a procedure, retraction may include large-scale movement as well as minor position adjustments and small reciprocal motions. Different types of movements may benefit from different rates and degrees of change in rigidity of the elongate device 310. For example, smaller movements may benefit from relatively smaller and slower changes in rigidity to avoid unexpected changes in the orientation of the distal portion of the elongate device 310. Accordingly, in the following examples, a system may adjust rigidity or other properties of the flexible elongate device 310, which may be performed repeatedly during the course of a procedure.

Figure 3:
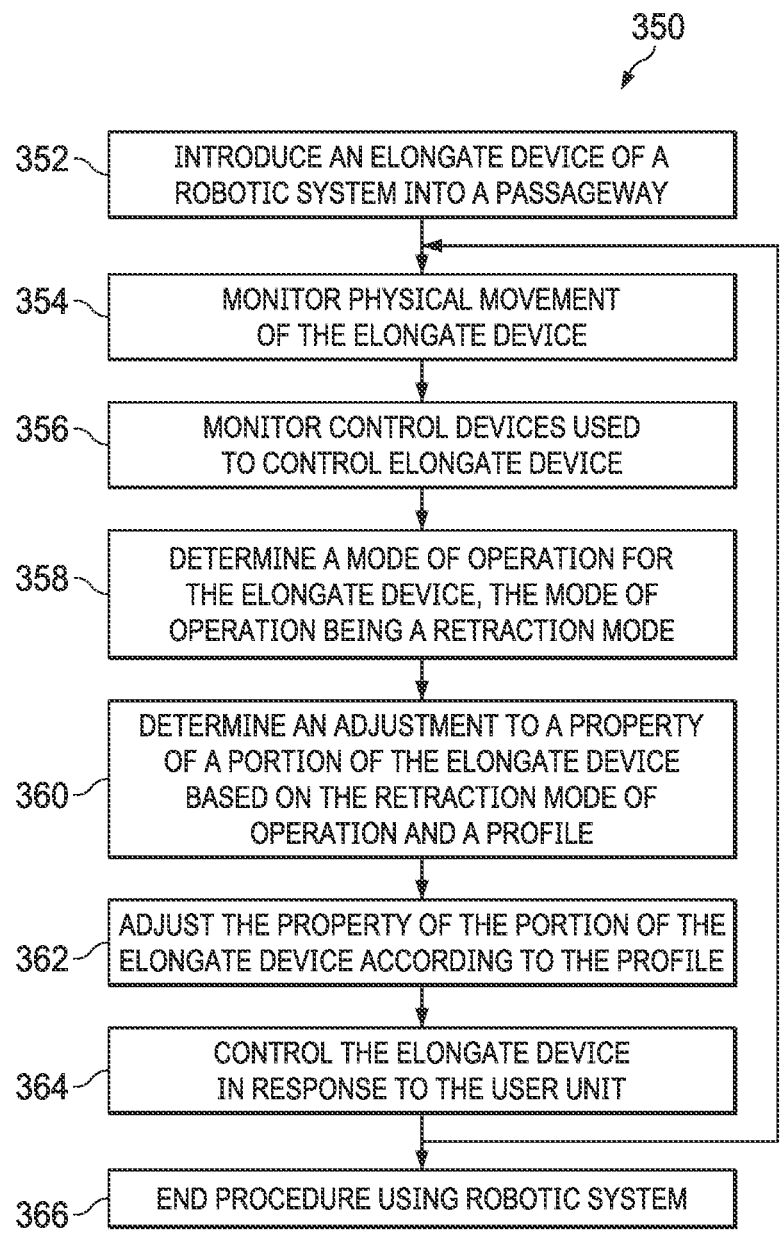
FIG. 3 is a flowchart illustrating a method of controlling an elongate device using a retraction mode according to some embodiments.

Retraction of the elongate device 310 is described first, and examples of advancing the elongate device 310 follow. FIGS. 3 and 4A-4F illustrate an elongate device 310 of a robotic medical system being retracted and the system reducing the rigidity of the elongate device 310 accordingly. FIG. 3 is a flowchart describing a method 350 of controlling an elongate device in a retraction mode according to some embodiments. The method 350 is illustrated in FIG. 3 as a set of operations or processes. The processes illustrated in FIG. 3 may be performed in a different order than the order shown in FIG. 3, and one or more of the illustrated processes might not be performed in some embodiments of method 350. Additionally, one or more processes that are not expressly illustrated in FIG. 3 may be included before, after, in between, or as part of the illustrated processes. The method may be performed by a system—such as the robotic medical system 100 described above—and in some embodiments, one or more of the processes of method 350 may be implemented, at least in part, in the form of executable code stored on non-transitory, tangible, machine-readable media that, when run by one or more processors (e.g., the processors of the control system 112 above) of the system, may cause the one or more processors to perform one or more of the processes. FIGS. 4A-4F are simplified diagrams of the robotic medical system 100 including the steerable elongate device 310 at various points during the method 350 according to some embodiments.

Referring to process 352 of FIG. 3, in some examples, an elongate device (e.g., the elongate device 310 as shown in FIG. 4A) may be introduced into a passageway, such as an anatomic passageway. Example anatomic passageways may include portions of the intestines, the kidneys, the brain, the heart, the circulatory system, lungs, urethras, arteries, umbilical lines, and/or the like.

Referring to process 354, the control system 112 of the robotic system 100 may monitor physical movement of the elongate device 310. Monitoring may occur continuously, periodically, and/or at set times. Accordingly, process 354 may be performed concurrently with other processes in method 350.

For detecting retraction, the control system 112 may monitor the position of any number of points on the elongate device 310 (e.g., a point 402, a proximal point along the elongate device, a distal point along the elongate device, etc.), on a body to which the device is coupled, and/or on an instrument extending through the elongate device. The control system 112 may capture the position of each of these points in order to detect retraction from a latched position represented by a marker 404, as described further below. The positions may be measured by a sensor system—such as sensor system 108—using any suitable set of sensors including position sensors, shape sensors—such as shape sensor 314—and/or other suitable position measuring devices. For example and with reference to FIG. 2A-B, a sensor device 320 may be used to measure movement of an instrument body 312 as the instrument body 312 moves on an insertion stage 308 along an insertion axis A. The system may use the sensor device 320 to monitor changes in the insertion depth of the elongate device. Additionally or in the alternative, monitoring may include measuring positions or forces supplied by one or more actuators coupled to cables, linkages, pull wires, tendons, or other steering controls within the elongate device and used to steer the elongate device.

Monitoring movement of the elongate device may also include monitoring velocity of one or more points on the elongate device 310, such as point 402. For example, the system may record position measurements over time with which to calculate the amount of movement and/or the velocity. The system may also monitor and record other state properties in the course of monitoring, such as current time and/or a current control configuration (e.g., current rigidity caused by closed-loop steering wire control) of the elongate device. Where the control configuration relates to an adjustable property of the elongate device, such as rigidity, the system may consider previous adjustments made to the property to determine present values.

Referring to process 356 of FIG. 3, the control system 112 may monitor control devices that an operator O may use to control the elongate device 310. These control devices may include the control devices of the master assembly 106, and in various examples, the control devices may include a joystick, a trackball, a scroll wheel, a directional pad, a button, a data glove, a trigger-gun, a hand-operated controller, a voice recognition device, a body motion or presence sensor, and/or other suitable control device. The monitoring of process 356 may be performed concurrently with other processes in method 350. For example, in the course of monitoring, the control system 112 may receive a user input that instructs the system to move the elongate device along an insertion axis A and/or user input that instructs the system to articulate the elongate device to steer it in a degree of freedom other than along the insertion axis.

Referring to process 358, the control system 112 may determine a mode of operation based on the physical movement monitored in process 354, the user input received in process 356, and/or other suitable factors. In the examples that follow, the elongate device 310 may have an active mode and a retraction mode of operation, and the determination may identify the retraction mode. Further examples where the determination identifies the active mode are described with reference to a subsequent figure.

The control system 112 may determine the retraction mode based on the physical movement of the elongate device (e.g., as monitored in process 354) and/or the user input (e.g., as monitored in process 356). With respect to physical movement, the control system 112 may determine the retraction mode of operation based on a reference point 402 of the elongate device 310 being retracting more than a threshold distance (e.g., 5 mm, 10 mm, etc.) from a position (e.g., a latched position 404, which may be recorded at the conclusion of the most recent forward motion). In some examples, the control system 112 may determine the retraction mode of operation based on a retraction velocity of the elongate device 310 exceeding a threshold velocity (e.g., 0.1 mm/s, 5 mm/s, etc.). In some examples, the control system 112 may determine the retraction mode of operation based on the reference point 402 retracting for an amount of time that exceeds a threshold time (e.g., 1 second, 10 seconds, etc.). The threshold distance, threshold velocity, or threshold time may be predetermined thresholds.

In some examples, the control system 112 may take into account perturbations, sensed noise, cyclic anatomic motion (e.g., respiration and cardiac motion), movement within an anatomy, other movement caused by environmental displacement, and/or combinations thereof. In some embodiments, these external effects may be filtered from the monitored data to isolate physical movement of the elongate device relative to the passageway. This may allow the amount of advancement or retraction to be measured even if the patient moves. Furthermore, in some embodiments, these external effects may themselves trigger a response from the system, even if there is no relative movement of the elongate device relative to the passageway. For example, the control system 112 may select the retraction mode of operation when a cough, spasm, or other movement of the patient is detected, even if the elongate device does not move relative to the patient.

With respect to determining a mode of operation based on user input, the control system 112 may select the retraction mode of operation based on any suitable aspect of the user input of process 356. In some examples, the system may determine the retraction mode based on user input commanding motion in the retracting direction at a velocity greater than a threshold velocity (e.g., 0.1 mm/s, 5 mm/s, etc.). In some examples, the system may determine the retraction mode based on user input commanding motion in the retracting direction for longer than a threshold time (e.g., 1 second, 10 seconds, etc.). The threshold velocity or threshold time may be predetermined thresholds. In some examples, the system may determine the retraction mode of operation based on the amount of pressure placed on an input device and/or loss of contact between the operator's hand and the input device.

Where the user input(s) command motion in more than one degree of freedom, the degrees of freedom may be prioritized. In some examples, priorities may be based on patient safety. For example, a first user input that commands a retracting motion may have priority over a second user input that commands a steering motion so that the system selects the retraction mode based on the retracting motion regardless of any steering motion. This may avoid forcing a flexed elongate device back through the passageway. In some such examples, the first user input that commands a retraction motion may be given priority over the second user input that commands steering if the size, speed, and/or velocity of the first input exceeds a threshold. Accordingly, the system may select the retraction mode based on the retracting motion of the first user input regardless of any steering motion if the first user input exceeds the threshold.

Where the monitored motion of process 354 and the user inputs of process 356 conflict, the system may utilize any suitable rule or heuristic to determine the appropriate response. In some examples, if either the motion of the elongate device or any of the user inputs satisfy any of the above-noted conditions for the retraction mode, the system may select the retraction mode regardless of the remainder of the motion and/or the input(s). This may provide a failsafe that places the elongate device in the retraction mode when there is any indication of retraction. In some examples, the motion of the elongate device may be prioritized over the user input, so that the system selects the retraction mode if the elongate device is physically retracted, without concern for the user input. This may allow for an appropriate response if the elongate device is retracted (and, in some cases, advanced) manually by hand or by other processes.

When the elongate device transitions between modes, the system may record state properties such as position, time, control configuration, etc. As a change from active mode to retraction mode may indicate the conclusion of the most recent forward motion, the system may record the positions of the reference point(s) 404 when the mode changes for use in the comparisons described above.

Referring to process 360, the control system 112 may determine an adjustment to a property—such as radial rigidity or axial rigidity—of the elongate device 310 based on the retraction mode of operation and one or more profiles associated with the retraction mode. The profile(s) may specify how much to adjust a property of a portion of the elongate device, how quickly to adjust the property, upper and/or lower bounds for the adjustment, and/or other suitable aspects. The profile(s) may be based on any of the considerations described in the context of process 358, and the considerations that determine a mode of operation may be the same or different from the considerations that determine how much to adjust, how quickly to adjust, etc. The system may apply any number of profiles for a given property and mode of the elongate device, and different profiles may be used at different stages of a procedure.

In various examples, a profile may relate to rigidity and may utilize any number of suitable factors for determining a rigidity for the elongate device 310 in the retraction mode. Illustrative factors include: amount of retraction from a latched position, velocity of retraction, duration of retraction, total insertion depth, location as a percentage of current maximum insertion depth, size of an operator input, speed of an operator input, velocity of an operator input, duration of an operator input, and/or pressure or lack thereof on an input device. The factors may include an amount by which a reference point 402 of the elongate device 310, a body to which the device is coupled, and/or an instrument extending through the elongate device is retracted from a position 404 latched at the conclusion of the most recent forward motion. For factors based on motion of the elongate device (e.g., as monitored in process 354), the system may take into account perturbations, sensed noise, cyclic anatomic motion (e.g., respiration and cardiac motion), movement within an anatomy, other movement caused by environmental displacement, and/or combinations thereof. The factors may also include external forces applied to the elongate device, a shape of the elongate device, sensitivity of anatomy forming a passageway, a curvature of the anatomy, an operator preference, and/or other suitable factors.

Where factors conflict, as in the above example, the system may utilize any suitable rule or heuristic to determine the appropriate response. In some examples, the factor that results in the least rigidity may govern. For example, when motion of the elongate device would produce a first degree of rigidity and when the first user input would produce a second degree of rigidity, the system may implement the lesser of the two. In some examples, factors based on real-world motion of the elongate device may govern over factors based on user inputs so that the system implements a degree of rigidity based on the motion of the elongate device where there is conflict.

The profile may include any combination of linear, non-linear, exponential, logarithmic, step, piece-wise, hyperbolic, parabolic, periodic/trigonometric, inverse hyperbolic, polynomial, modular, other monotonic functions, and/or the like that define the relationship between the property (e.g., rigidity) and the factors that determine the property. In some embodiments, the profile may depends on derivatives, integrals, or other functions of the relevant factors. In some embodiments, the profile may have a stepwise configuration with no rigidity adjustment until a threshold is met, followed by a full slackening after the threshold is reached.

A profile may be organized into different regions of different behavior. An example profile may include a first region in which a one or more (e.g., a set of) factors have not yet exceeded a predetermined threshold, a second region in which the rigidity is reduced in proportion to the factor(s), and a third region in which the rigidity is reduced to a lower value (e.g., a minimum value). The minimum value may be set at a nominal, possibly non-zero value, to retain at least some control over a bend in the distal portion of the elongate device, an instrument deployed at the distal portion of the elongate device, and/or the like. Minimums and maximums may be determined in part by a physical limit of the actuators, the steering controls, the elongate device, a body to which the elongate device is coupled, and/or the instrument. In some examples, a maximum rate may be configured to avoid elastic rebound, buckling or bunching of the steering controls, or other effects of the actuators or steering controls.

Referring to process 362, the control system 112 may adjust the property of the portion of the elongate device according to the adjustments and/or profiles as determined in process 360. The profiles may govern both the final value and the rate at which changes are made. In some examples, the control system 112 may adjust the rigidity of a distal portion of the elongate device 310 to a value determined by the profile by adjusting forces applied by actuators to steering controls of the elongate device. In some such examples, the control system 112 may adjust the force and/or torque applied by the actuators to control the pushing and/or pulling of one or more wires within the elongate device. When adjusting a force and/or torque applied by the actuators, the control system 112 may implement a scaling factor and/or torque multiplier used to scale a force and/or torque that is applied by the actuators. In activating the actuators, the control system 112 may consider an external force applied to the elongate device, a shape of the elongate device, the sensitivity of the anatomy forming the passageways, the curvature of the anatomy, one or more operator preferences, and/or other considerations.

Referring to process 364, when the control system 112 detects a user input in process 356, the control system 112 may control the elongate device in response to the user input. In some embodiments, the control system 112 may cause an insertion stage to retract the elongate device along the insertion axis in response to the user input. In some embodiments, the control system 112 may cause actuators to apply force to cables, linkages, pull wires, tendons, or other steering controls within the elongate device in response to the user input.

Some aspects of how the system controls the elongate device may be determined based on the property of the portion of the elongate device adjusted in process 362. For example, the system may change how much or how quickly the elongate device is retracted based on the rigidity of the portion of the elongate device. For example, the system may set a retraction velocity limit based on the current rigidity, a rate at which the rigidity is currently being reduced, and/or a maximum rate at which the rigidity can be reduced. This may allow the system to retract the elongate device more quickly when there is little risk of injury to the passageway. In further examples, the system changes how much or how quickly the elongate device is articulated in the other degrees of freedom based on the property adjusted in process 362.

The system 100 may perform one or more of the monitoring, determinations, adjustments, or control of processes 354-364 repeatedly throughout the procedure to provide real-time or near real-time response in the elongate device 310 before concluding in process 366. During a procedure, the mode of operation for the elongate device may switch between a retraction mode and an active mode. As explained above and will be explained in further detail below, the system may determine the appropriate adjustment to properties of the elongate device (e.g., rigidity) based on the mode of operation and/or one or more profiles associated with the mode of operation.

The method 350 will now be explained in the context of a robotic procedure. For example, the elongate device 310 may begin in an active mode and have a certain degree of rigidity as illustrated in FIG. 4A. As illustrated in FIG. 4B, the control system 112 may keep the elongate device 310 in the active mode while the elongate device 310 is retracted up until the amount of retraction (measured or user-instructed) or the retraction velocity (measured or user-instructed) reaches a threshold. In this example, the control system 112 may keep the rigidity shown in FIG. 4B the same as in FIG. 4A, although in other examples, user input while in the active mode may cause changes in the rigidity. As illustrated in FIG. 4C, the control system 112 may determine that the point 402 of the elongate device 310 has retracted from the latched position 404 by more than a threshold amount or has been instructed to do so, and the control system 112 may reduce the rigidity of the elongate device 310 at a rate according to the profile. The rate and/or final rigidity specified by the profile may depend on a number of factors such as the amount that the elongate device 310 has been withdrawn, the retraction velocity of the elongate device 310, the amount of time that the elongate device 310 has been in the retraction mode, and/or other suitable factors. For example, when the elongate device 310 is retracted or commanded to retract at a slower rate as shown in FIG. 4C, the rigidity may be reduced at a slower rate according to the profile.

Referring to FIGS. 4D-4F, when the elongate device 310 is retracted or commanded to retract at a faster rate, the rigidity may be reduced at a faster rate according to the profile. In that regard, FIG. 4D corresponds to FIG. 4A and illustrates the elongate device 310 in the active mode before retraction. FIG. 4E corresponds to FIG. 4B and illustrates the elongate device 310 in the active mode because the amount of retraction and/or the retraction velocity have not yet reached the respective threshold(s). FIG. 4F corresponds to FIG. 4C and illustrates the control system 112 determining that the point 402 of the elongate device 310 has retracted by more than a threshold amount or has been instructed to do so. The control system 112 may reduces the rigidity of the elongate device 310 at faster rate than that of FIG. 4C due to the faster retraction velocity (measured or user-instructed).

In some examples, if the control system 112 determines that the elongate device 310 is retracting or instructed to retract at an even greater retraction velocity, the rigidity may be reduced at the greater rate (e.g., the system 100 transitions from FIG. 4D to FIG. 4F) regardless of the amount that the elongate device 310 has been retracted.

During the course of a procedure, processes of the method 350 may be repeated multiple times, and the states and responses illustrated in FIGS. 4A-4F may occur multiple times and in any order. For example, the control system 112 may maintain the rigidity of the elongate device 310 during a first time interval based on the motion and/or user input in the first interval, reduce the rigidity of the elongate device 310 at a first rate (e.g., as illustrated in FIG. 4C) during a second time interval based on the motion and/or user input in the second interval, and reduce the rigidity during a third time interval based on the motion and/or user input in the third time interval.

Figure 5:
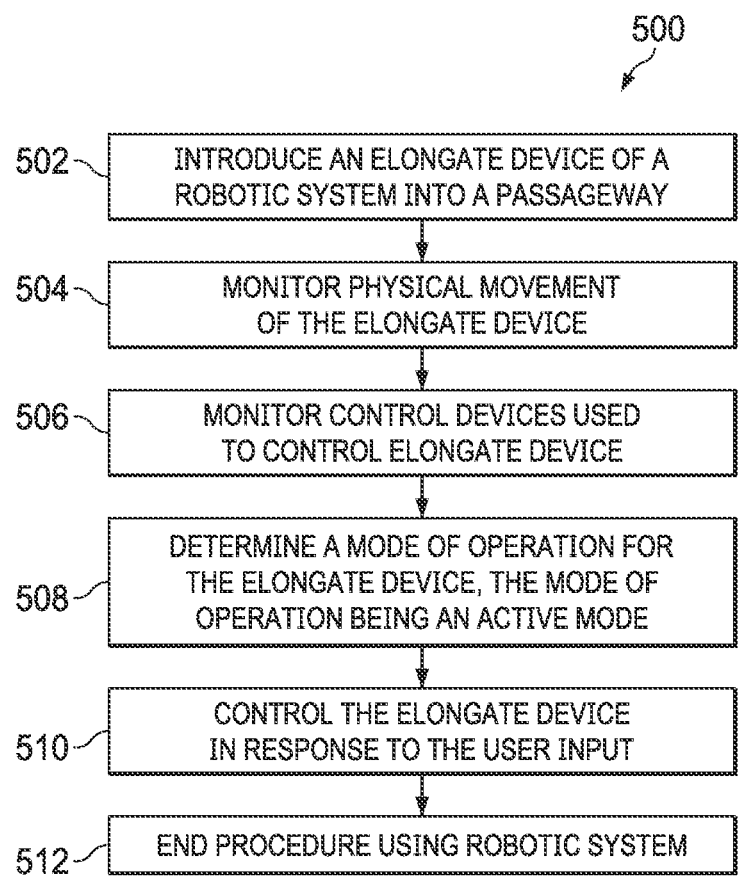
FIG. 5 is a flowchart illustrating a method of controlling an elongate device using an active mode according to some embodiments.

Some of the above examples describe operation in the retraction mode. FIG. 5 is a flowchart describing a method 500 of controlling an elongate device in an active mode according to some embodiments. The method 500 is illustrated in FIG. 5 as a set of operations or processes. The processes illustrated in FIG. 5 may be performed in a different order than the order shown in FIG. 5, and one or more of the illustrated processes might not be performed in some embodiments of method 500. Additionally, one or more processes that are not expressly illustrated in FIG. 5 may be included before, after, in between, or as part of the illustrated processes. The method may be performed by a system—such as the robotic medical system 100 described above—and in some embodiments, one or more of the processes of method 500 may be implemented, at least in part, in the form of executable code stored on non-transitory, tangible, machine-readable media that, when run by one or more processors (e.g., the processors of the control system 112 above) of the system, may cause the one or more processors to perform one or more of the processes. The method 500 may be performed in combination with method 350 in an alternating fashion during the course of a procedure.

Referring to process 502, in some examples, the elongate device is introduced into a passageway. Referring to process 504, the control system 112 of the robotic system 100 may monitor physical movement of the elongate device, and referring to process 506, the control system 112 may monitor control device(s) used to control the elongate device. Processes 504 and 506 may be performed substantially as described in processes 354 and 356, respectively.

Referring to process 508, the control system 112 may determine a mode of operation based on the physical movement of the elongate device monitored in process 504, the user input monitored in process 506, and/or other suitable factors. In the examples that follow, the elongate device 310 may have an active mode and a retraction mode or operation, and the determination may identify the active mode of operation.

Some aspects of physical movement of the elongate device 310 monitored in process 504 that may cause the control system 112 to select the active mode include advancing motion of the elongate device 310 as well as some types of retracting motion. For example, the control system 112 may select the active mode when the elongate device 310 retracts by less than a threshold amount and a retraction velocity is below a threshold. In further examples, the control system 112 may select the active mode when the elongate device has been inert or not retracting for a period of time.

Similarly, with respect to the user input monitored in process 506, the control system 112 may select the active mode when user input commands the elongate device to advance or commands an amount of retraction that is less than a threshold and a retraction velocity that is less than a threshold. The control system 112 may also consider the axis associated with the user input. The control system 112 may select the active mode of operation when a user input commands articulation of the elongate device in a degree of freedom other than along the insertion axis, e.g., provided that the user input does not also command a retraction motion greater than a threshold. For example, the control system 112 may select the active mode if the operator O attempts to steer the elongate device without retracting it.

Where the monitored motion of process 504 and the user inputs of process 506 conflict, the system may utilize any suitable rule or heuristic to determine the appropriate response.

Referring to process 510, when the control system 112 detects a user input (e.g., in process 506), the control system 112 may control the elongate device in response to the user input. In some embodiments, the control system 112 may cause an insertion stage to advance or retract the elongate device along the insertion axis in response to the user input. In some embodiments, the control system 112 may cause actuators to apply force to cables, linkages, pull wires, tendons, or other steering controls within the elongate device in response to the user input. In contrast to the retraction mode, in the active mode, the control system 112 may maintain the rigidity of the elongate device 310 or increase it while controlling the elongate device in process 510.

The system 100 may perform one or more of the monitoring, determinations, adjustments, or control of processes 504-510 repeatedly, alone or in combination with one or more of the processes of method 350, before concluding in process 512. For example, during a procedure, the mode of operation for the elongate device may switch between the retraction mode and the active mode, and the system may determine the appropriate adjustment to properties of the elongate device (e.g., rigidity) based on the mode of operation and/or one or more profiles associated with the mode of operation.

In these examples and others, the system may provide both rapid and fine-grained control of various properties of the elongate device including rigidity and may provide additional protection against damage to the passageway in which the elongate device is inserted.

Various Examples of Implementations of the Disclosure

This disclosure describes various instruments and portions of instruments in terms of their state in three-dimensional space. For example, the term position refers to the location of an object or a portion of an object in a three-dimensional space (e.g., three degrees of translational freedom along Cartesian x-, y-, and z-coordinates). The term orientation refers to the rotational placement of an object or a portion of an object (e.g., one or more degrees of rotational freedom, such as roll, pitch, and yaw). The term pose refers to the position of an object or a portion of an object in at least one degree of translational freedom and to the orientation of that object or portion of the object in at least one degree of rotational freedom (e.g., up to six total degrees of freedom). The term shape refers to a set of poses, positions, or orientations measured along an object.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Medical tools may be delivered through the flexible elongate devices (e.g., catheters) disclosed herein and may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls that extend between its proximal and distal portions to controllably bend the distal portion of a medical tool. Steerable instruments are described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. patent application Ser. No. 12/286,644 (filed Sep. 30, 2008 and titled "Passive Preload and Capstan Drive for Surgical Instruments"), which are incorporated by reference herein in their entireties.

The systems described herein may be suited for navigation and treatment of anatomic tissues, via natural or surgically created passageways, in any of a variety of anatomic systems, including the lung, colon, intestines, kidneys and kidney calices, brain, heart, circulatory system including vasculature, and/or the like.

Note that the processes and displays presented might not inherently be related to any particular computer or other apparatus. Various general-purpose systems may be used with programs in accordance with the teachings herein, or it may prove convenient to construct a more specialized apparatus to perform the operations described. In addition, it will be appreciated that a variety of programming languages may be used to implement the examples described herein.

While certain examples have been described and shown in the accompanying drawings, it is to be understood that such examples are merely illustrative of and are not restrictive, and that the described examples are not limited to the specific constructions and arrangements shown and described, since various other modifications may occur to those ordinarily skilled in the art.

What is claimed is:
1. A robotic system comprising:
a manipulator assembly configured to drive an elongate device;
a control device configured to receive user input commanding the elongate device; and
a control system communicatively coupled to the manipulator assembly and the control device, the control system configured to:
monitor movement of the elongate device during a plurality of intervals;
monitor user input received by the control device during the plurality of intervals;

adjust a property of the elongate device based on at least one of the monitored movement or the monitored user input, wherein adjustment of the property includes operations to:
   based on at least one of movement or user input during a first interval of the plurality of intervals, keep the property of the elongate device substantially the same during the first interval;
   based on at least one of movement or user input during a second interval of the plurality of intervals, adjust the property of the elongate device at a first rate during the second interval; and
   based on at least one of movement or user input during a third interval of the plurality of intervals, adjust the property of the elongate device at a second rate that is greater than the first rate during the third interval.

2. The robotic system of claim 1, wherein the property includes a rigidity of the elongate device, and wherein the control system is configured to reduce the rigidity of the elongate device at the first rate during the second interval and to reduce the rigidity of the elongate device at the second rate during the third interval.

3. The robotic system of claim 2, wherein the control system is configured to keep the rigidity substantially the same during the first interval based on retraction of the elongate device being less than a threshold.

4. The robotic system of claim 3, wherein the control system is configured to reduce the rigidity of the elongate device at the first rate during the second interval and to reduce the rigidity of the elongate device at the second rate during the third interval based on retraction of the elongate device being greater than the threshold.

5. The robotic system of claim 3, wherein the control system is configured to reduce the rigidity of the elongate device at the first rate during the second interval based on a retraction velocity of the elongate device being less than a second threshold and to reduce the rigidity of the elongate device at the second rate during the third interval based on the retraction velocity of the elongate device being greater than the second threshold.

6. The robotic system of claim 2, wherein the control system is configured to keep the rigidity substantially the same during the first interval based on user input commanding the elongate device to retract less than a threshold.

7. The robotic system of claim 6, wherein the control system is configured to reduce the rigidity of the elongate device at the first rate during the second interval and to reduce the rigidity of the elongate device at the second rate during the third interval based on user input commanding the elongate device to retract more than the threshold.

8. The robotic system of claim 6, wherein the control system is configured to reduce the rigidity of the elongate device at the first rate during the second interval based on user input commanding the elongate device to retract at a velocity less than a second threshold and to reduce the rigidity of the elongate device at the second rate during the third interval based on user input commanding the elongate device to retract at a velocity greater than the second threshold.

9. The robotic system of claim 1, wherein the control system is configured to adjust the property of the elongate device based on at least one of: an amount of retraction from a latched position, a velocity of retraction, a duration of retraction, a total insertion depth, a location as a percentage of current maximum insertion depth, a size of a user input, a speed of a user input, a velocity of a user input, a duration of a user input, or pressure on the control device.

10. The robotic system of claim 1, wherein the control system is configured to prioritize the monitored movement of the elongate device over the monitored user input.

11. The robotic system of claim 1, wherein the control system is configured to determine a mode for the elongate device based on at least one of the monitored movement or the monitored user input.

12. The robotic system of claim 11, wherein determination of the mode includes operations to:
   determine an active mode based on retraction of the elongate device being less than a threshold; and
   determine a retraction mode based on retraction of the elongate device being greater than the threshold.

13. The robotic system of claim 12, wherein determination of the mode includes operations to:
   determine the retraction mode based on a retraction velocity of the elongate device being greater than a second threshold.

14. The robotic system of claim 11, wherein determination of the mode includes operations to:
   determine an active mode based on the user input commanding retraction of the elongate device less than a threshold; and
   determine a retraction mode based on the user input commanding retraction of the elongate device more than the threshold.

15. The robotic system of claim 14, wherein determination of the mode includes operations to:
   determine the retraction mode based on the user input commanding a retraction velocity greater than a second threshold.

16. The robotic system of claim 14, wherein determination of the mode includes operations to:
   determine the active mode based on the user input commanding advancement along an insertion axis; and
   determine the active mode based on the user input commanding movement along a degree of freedom other than the insertion axis without retraction along the insertion axis.

17. The robotic system of claim 1, wherein the manipulator assembly includes an insertion stage configured to drive a device body to which the elongate device is coupled, and wherein the control system is further configured to monitor the movement by monitoring movement of the device body along the insertion stage.

18. The robotic system of claim 1, wherein the control system is further configured to:
   based on a rigidity of the elongate device, limit a retraction velocity of the elongate device in response to the user input.

19. The robotic system of claim 1, wherein the control system is further configured to limit a retraction velocity of the elongate device based on a maximum rate of change of rigidity of the elongate device.

20. A method comprising:
   monitoring movement of an elongate device;
   receiving user input commanding motion of the elongate device;
   determining a mode of operation based on at least one of the monitored movement or the received user input; and
   adjusting a property of the elongate device based on a profile associated with the mode of operation, wherein the adjusting the property of the elongate device includes:

maintaining the property of the elongate device substantially the same during a first interval;
adjusting the property of the elongate device at a first rate during a second interval; and
adjusting the property of the elongate device at a second rate that is different from the first rate during a third interval.

\* \* \* \* \*